US010067117B2

(12) United States Patent
Tyler et al.

(10) Patent No.: US 10,067,117 B2
(45) Date of Patent: Sep. 4, 2018

(54) CELL-BASED BIOSENSOR ARRAY AND ASSOCIATED METHODS FOR MANUFACTURING THE SAME

(71) Applicant: Axion BioSystems, Inc., Atlanta, GA (US)

(72) Inventors: Phillip Edward Tyler, Decatur, GA (US); Swaminathan Rajaraman, Atlanta, GA (US); Amanda Jervis Preyer, Atlanta, GA (US)

(73) Assignee: Axion BioSystems, Inc., Atlanta, GA (US)

( * ) Notice: Subject to any disclaimer, the term of this patent is extended or adjusted under 35 U.S.C. 154(b) by 297 days.

(21) Appl. No.: 14/825,140

(22) Filed: Aug. 12, 2015

(65) Prior Publication Data

US 2016/0047770 A1 Feb. 18, 2016

Related U.S. Application Data

(60) Provisional application No. 62/036,149, filed on Aug. 12, 2014.

(51) Int. Cl.
*G01N 33/483* (2006.01)
*B01L 3/00* (2006.01)

(52) U.S. Cl.
CPC ........ *G01N 33/4836* (2013.01); *B01L 3/5085* (2013.01)

(58) Field of Classification Search
CPC .................................................. G01N 33/4836
See application file for complete search history.

(56) References Cited

U.S. PATENT DOCUMENTS 4,806,432 A 2/1989 Eguchi et al.
5,965,452 A 10/1999 Kovacs
(Continued)

FOREIGN PATENT DOCUMENTS

CN 102156158 A 8/2011
JP 11-187865 A 7/1999
(Continued)

OTHER PUBLICATIONS

Agar, J.C. et al., "Novel PDMS(silicone)-in-PDMS(silicone): Low Cost Flexible Electronics without Metallization," 2010 Electronic Components and Technology Conference, pp. 1226-1230, 2010.
(Continued)

*Primary Examiner* — Jonathan M Hurst
(74) *Attorney, Agent, or Firm* — Meunier Carlin & Curfman LLC (57) ABSTRACT

A cell-based biosensor array includes a base plate having a plurality of substantially transparent areas. The cell-based biosensor array also includes a flexible substrate coupled to the base plate and having disposed thereon a plurality of electrode sets, a plurality of terminal contacts, and a plurality of conductive traces. Each electrode set is disposed proximate a respective one of the substantially transparent areas, and each electrode set includes at least one electrode configured to detect an electric signal. Each terminal contact is associated with a respective one of the at least one electrode and disposed proximate a perimeter of the flexible substrate. Each conductive trace is electrically coupling a respective at least one electrode to the corresponding terminal contact. A first portion of flexible substrate including the electrode sets is disposed on a first surface of the base plate. A second portion of the flexible substrate including the terminal contacts is disposed on a second surface of the base plate.

18 Claims, 9 Drawing Sheets

(56) References Cited

U.S. PATENT DOCUMENTS

| | | | |
|---|---|---|---|
| 6,051,422 | A | 4/2000 | Kovacs et al. |
| 6,132,683 | A | 10/2000 | Sugihara et al. |
| 6,315,940 | B1 | 11/2001 | Nisch et al. |
| 6,352,853 | B1 | 3/2002 | King et al. |
| 6,376,233 | B1 | 4/2002 | Wolf et al. |
| 6,969,449 | B2 | 11/2005 | Maher et al. |
| 7,169,609 | B2 | 1/2007 | Negulescu et al. |
| 7,192,752 | B2 | 3/2007 | Xu et al. |
| 7,267,751 | B2 | 9/2007 | Gelbart et al. |
| 7,470,533 | B2 | 12/2008 | Xu et al. |
| 7,981,362 | B2 | 7/2011 | Glezer et al. |
| 8,000,804 | B1 | 8/2011 | Wessendorf et al. |
| 8,227,223 | B2 | 7/2012 | Giaever et al. |
| 8,361,385 | B2 | 1/2013 | Glezer et al. |
| 8,420,363 | B2 | 4/2013 | Wang et al. |
| 8,460,921 | B2 | 6/2013 | Gross |
| 2002/0025568 | A1* | 2/2002 | Maher ............... G01N 33/5008 435/173.6 |
| 2002/0192120 | A1 | 12/2002 | DeSilets et al. |
| 2005/0006234 | A1 | 1/2005 | Hassibi |
| 2006/0018833 | A1 | 1/2006 | Murphy et al. |
| 2006/0057771 | A1* | 3/2006 | Kovacs ............. G01N 33/4836 438/106 |
| 2006/0135862 | A1 | 6/2006 | Tootle et al. |
| 2007/0178579 | A1 | 8/2007 | Ross et al. |
| 2007/0223935 | A1* | 9/2007 | Asai ........................ G02B 6/43 398/164 |
| 2009/0004754 | A1 | 1/2009 | Oldenburg |
| 2009/0177144 | A1 | 7/2009 | Masmanidis et al. |
| 2009/0297913 | A1 | 12/2009 | Zhang et al. |
| 2010/0120626 | A1 | 5/2010 | Ross et al. |
| 2013/0123139 | A1 | 5/2013 | Kim et al. |
| 2013/0307520 | A1 | 11/2013 | Yen et al. |

FOREIGN PATENT DOCUMENTS

| | | |
|---|---|---|
| JP | 2003-515133 A | 4/2003 |
| JP | 2006-521550 A | 9/2006 |
| JP | 2007-532103 A | 11/2007 |
| JP | 2007-534927 A | 11/2007 |
| JP | 2008-534965 A | 8/2008 |
| JP | 2012-508051 A | 4/2012 |
| WO | 99/34202 A1 | 7/1999 |
| WO | 01/036958 A1 | 5/2001 |
| WO | 2004088536 A2 | 10/2004 |
| WO | 2005098425 A1 | 10/2005 |
| WO | 2006104839 A2 | 10/2006 |
| WO | 2010055287 A1 | 5/2010 |

OTHER PUBLICATIONS

American National Standards Institutes, Inc. (ANSI), Society for Laboratory Automation and Screening (SLAS), Footprint Dimensions, 2004.

American National Standards Institutes, Inc. (ANSI), Society for Laboratory Automation and Screening (SLAS), Height Dimensions, 2004.

American National Standards Institutes, Inc. (ANSI), Society for Laboratory Automation and Screening (SLAS), Bottom Outside Flange Dimensions, 2004.

American National Standards Institutes, Inc. (ANSI), Society for Laboratory Automation and Screening (SLAS), Well Positions, 2004.

American National Standards Institutes, Inc. (ANSI), Society for Laboratory Automation and Screening (SLAS), Well Bottom Elevation, 2011.

Bai, Q. et al., "Single-Unit Neural Recording with Active Microelectrode Arrays", IEEE Transactions on Biomedical Engineering, vol. 48, No. 8, pp. 911-920, 2001.

Blum, R.A. et al., "An Integrated System for Simultaneous, Multichannel Neuronal Stimulation and Recording", IEEE Transactions on Circuits and Systems, vol. 54, No. 12, pp. 2608-2618, 2007.

Brown, E.A. et al., "Stimulation and Recording of Neural Tissue, Closing the Loop on the Artifact", IEEE International Symposium on Circuits and Systems, pp. 356-359, 2008.

Brown, E.A. et al., "Stimulus-Artifact Elimination in a Multi-Electrode System", IEEE Transactions on Biomedical Circuits and Systems, vol. 2, No. 1, pp. 10-21, 2008.

Cetiner, B.A. et al., "Monolithic Integration of RF MEMS Switches with a Diversity Antenna on PCB Substrate", IEEE Transactions on Microwave Theory and Techniques, vol. 51, No. 1, pp. 332-335, 2003.

Cullen, D.K. et al., "Microfluidic engineered high cell density three-dimensional neural cultures", Journal of Neural Engineering, vol. 4, pp. 159-172, 2007.

Van Dijk, J.P. et al., "Corrigendum to 'Motor unit number estimation using high-density surface electromyography'", Clinical Neurophysiology, vol. 119, p. 2416, 2008.

French, R.H. et al., "Optical properties of polymeric materials for conenctrator photovoltaic systems", Solar Energy Materials & Solar Cells, vol. 95, pp. 2077-2086, 2011.

Ghodsian, B. et al., "Development of RF-MEMS Switch on PCB Substrates With Polyimide Planarization", IEEE Sensors Journal, vol. 5, No. 5, pp. 950-955, 2005.

Giovangrandi, L. et al., "Low-cost microelectrode array with integrated heater for extracellular recording of cardiomyocyte cultures using commercial flexible printed circuit technology", Sensors and Actuators B, vol. 113, pp. 545-554, 2006.

Gong, J. et al., "Two-Dimensional Digital Microfluidic System by Multi-Layer Printed Circuit Board", 18th IEEE International Conference on Micro Electro Mechanical Systems, pp. 726-729, 2005.

Heuschkel, M.O. et al., "A three-dimensional multi-electrode array for multi-site stimulation and recording in acute brain slices", Journal of Neuroscience Methods, vol. 114, pp. 135-148, 2002.

Joung, Y.H. et al., "Inter-substrate microstructure formation by electroplating bonding technology", Journal of Micromech. and Microeng., vol. 18, 2008.

Guo, L. et al., "A Low-Cost, Easy-Fabricating Stretchable Microneedle-Electrode Array for Intramuscular Recording and Stimulation", Proceedings of the 5th International IEEE EMBS Conference on Neural Engineering, pp. 562-565, 2011.

Guo, L. et al., "A PDMS-Based Integrated Stretchable Microelectrode Array (isMEA) for Neural and Muscular Surface Interfacing," IEEE Trans. on Biomed. Circuits and Syst., vol. 7, No. 1, pp. 1-10, Feb. 2013.

Lorenz, H. et al., "High-aspect-ratio, ultrathick, negative-tone near-UV photoresist and its applications for MEMS", Sensors and Actuators A, vol. 64, pp. 33-39, 1998.

Lorenz, H. et al., "Fabrication of photoplastic high-aspect ratio microparts and micromolds using SU-8 UV resist", Microsystem Technologies, vol. 4, pp. 143-146, 1998.

Metz, S. et al., "Microelectrodes with three-dimensional structures for improved neural interfacing", 2001 Proceedings of the 23rd Annual EMBS International Conference, IEEE, pp. 765-768, 2001.

Oka, H. et al., "A new planar multielectrode array for extracellular recording: application to hippocampal acute slice", Journal of Neuroscience Methods, vol. 93, pp. 61-67, 1999.

Rajaraman, S. et al., "Microfabrication technologies for a coupled three-dimensional microelectrode, microfluidic array", J. Micromech. Microeng., vol. 17, pp. 163-171, 2007.

Rajaraman, S. et al., "Three-Dimensional Metal Transfer Micromolded Microelectrode Arrays (MEAs) for In-vitro Brain Slice Recordings", Solid-State Sensors, Actuators and Microsystems Conference, 2007.

Ramadoss, R. et al., "RF-MEMS Capacitive Switches Fabricated Using Printed Circuit Processing Techniques", Journal of Microelectromechanical Systems, vol. 15, No. 6, pp. 1595-1604, 2006.

Rennaker, R.L. et al., "An economical multi-channel cortical electrode array for extended periods of recording during behavior", Journal of Neuroscience Methods, vol. 142, pp. 97-105, 2005.

(56) References Cited

OTHER PUBLICATIONS

Ross, J.D. et al., "Multielectrode Impedance Tuning: Reducing Noise and Improving Stimulation Efficacy", Proceedings of the 26th Annual Conference of the IEEE EMBS, pp. 4115-4117, 2004.
"Toxicity Testing in the 21st Century: A Vision and a Strategy", The National Research Council, National Academies Press, 2007.
Wise, K., "Silicon Microsystems for Neuroscience and Neural Prostheses: Interfacing with the Central Nervous System at the Cellular Level", IEEE Engineering in Medicine and Biology Magazine, pp. 22-29, 2005.
Yaradanakul, A. et al., "Uncooled Infrared Microbolometers on a Flexible Substrate", IEEE Transactions on Electron Devices, vol. 49, No. 5, pp. 930-933, 2002.
Morin, F. et al., "Constraining the connectivity of neuronal networks cultured on micro-electrode arrays with microfluidic techniques: A step towards neuron-based functional chips," Biosensors and Bioelectronics, vol. 21, pp. 1093-1100, 2006.
French, R.H. et al., "Optical Properties of Materials for Concentrator Photovoltaic Systems," Photovoltaic Specialists Conference (PSVC), 2009 34th IEEE, pp. 394-399, 2009.
Dunlop, J. et al., "High-throughput electrophysiology: an emerging paradigm for ion-channel screening and physiology," Nature Reviews Drug Discovery, vol. 7, pp. 358-368, 2008.
International Search Report and Written Opinion of the International Searching Authority for PCT/US2015/044925, dated Nov. 9, 2015.
Scott et al., "A microfluidic microelectrode array for simultaneous electrophysiology, chemical stimulation, and imaging of brain slices", Lab on a Chip: Miniaturisation for Chemistry, Physics, Biology, Materials Science and Bioengineering, vol. 13, No. 4, 2013, pp. 527-535.
Mohammed et al., "Microfluidic add-on for standard electrophysiology chambers", Lab on a Chip: Miniaturisation for Chemistry, Physics, Biology, Materials Science and Bioengineering, vol. 8, No. 7, 2008, pp. 1048-1055.
McConnell, E.R. et al., "Evaluation of multi-well microelectrode arrays for neurotoxicity screening using a chemical training set", NeuroToxicology 33, 2012, 1048-1057.
Johnstone, A.F.M. et al., "Microelectrode arrays: A physiologically based neurotoxicity testing platform for 21st century", NeuroToxicology 31, 2010, 331-350.

\* cited by examiner

CELL-BASED BIOSENSOR ARRAY AND ASSOCIATED METHODS FOR MANUFACTURING THE SAME

PRIORITY INFORMATION

This application claims priority to U.S. Provisional Application No. 62/036,149, filed Aug. 12, 2014, and incorporated herein in its entirety.

TECHNICAL FIELD

The present disclosure relates generally to multiwell, high-throughput biosensors arrays and, more particularly, to a multiwell Microelectrode Array (MEA) with a flexible circuit-based electrode array and multilayer interconnect.

BACKGROUND

In vitro, electrophysiology culture systems having microelectrode arrays (MEAs) can provide important insights into networks of electrically active cells. MEA-based electrophysiology culture systems can be configured to concurrently monitor single cell and network level activity over extended periods of time, without affecting the cell culture under investigation. Since their instrumental role in the 1993 landmark discovery of spontaneous waves in a developing retina, the variety and scope of MEA-based electrophysiology applications have dramatically expanded. Recently, for example, MEA-based electrophysiology culture systems have been used to investigate the suppression of epileptic activity and to study novel plasticity mechanisms in cultured neural networks. Advances in cell culture preparations have led to applications for MEA-based electrophysiology systems in the fields of drug screening, safety pharmacology, stem cell applications and biosensing.

Many conventional MEA systems use printed circuit board (PCB) technology or microfabrication technology or a combination of both techniques to fabricate the electrode array device. The PCB industry has been steadily evolving over the past 40 years. PCB processing is typically performed on large area substrates (e.g., panels that can be 12-inch by 18-inch or larger) outside the cleanroom. Accordingly, PCB processes tend to be more cost-efficient than microfabrication/microelectronic processes, however they produce larger feature sizes when compared to microfabrication processes. That said, complex devices can be created on rigid, flexible, and flex-rigid substrates using PCB technologies.

In general, the limits of PCB technology are characterized by the width of the lines and spaces (L/S) it can produce. These lines and spaces dictate the routing and density of the circuit on any layer of the final construction. Of course multiple layer routing can improve the density of the circuitry constructed, however having multiple layers entails additional fabrication steps and costs. The most common L/S capability of PCB fabrication facilities is 5 microinch or mil (1 mil=25.4 μm). With advanced processing capabilities, some vendors are able to achieve 3 mil L/S. Anything below 3 mils is difficult to achieve in a repeatable and scalable fashion. Some vendors offer 1-2 mil L/S, but this requires an advanced process tool set, which typically results in much higher costs. In order to develop a high-density, high-throughput MEA with single layer processing, a smallest feature size of 1 mil L/S is required. Additionally, transparent substrates (for enabling optical recording and stimulation with inverted microscopy), such as polyethylene terephthalate (PET), are typically uncommon in PCB technology. The typical substrate for PCBs is opaque FR-4 (a glass reinforced epoxy resin) or Kapton (a translucent polyimide), on which copper traces and insulating materials are applied during subsequent processes. PCB technology is a great option for many industrial applications but it has limitations for suitability toward transparent, high-throughput MEAs.

There are numerous methods to fabricate a transparent microelectrode array. A traditional, monolithic approach, typically involves surface micromachining on biocompatible transparent substrates. The microfabrication process starts with the definition of electrically conductive throughholes (called vias) in the substrate that ensure front to back connectivity—the microelectrodes are defined on the front side and the electronics access points are on the backside of the substrate. These through-holes for the vias are typically created using one or more of the following techniques: computer numerically controlled (CNC) micromilling, laser micromachining, injection molding, etching, powder blasting, among others. Conductivity of the via is typically achieved by filling the through-hole with a conductive material, such as a conductive paste using techniques such as screen printing, stencil printing, squeegee printing, inkjet printing and/or metal via electrodeposition, electroless plating, sputtering, or evaporation. Once the vias are sufficiently filled to ensure an ohmic contact between the top and bottom sides, the topside circuitry can be patterned using traditional metallization/metal definition techniques such as metal lift-off, deposit and etch, electroplating utilizing photoresist molds, metal-transfer processes, or embossing. The transparent MEA device is completed by the application of an insulation layer to define the microelectrodes.

Although the use of vias facilitates interconnect paths through (and between) multiple layers of a substrate, fabricating vias is both challenging and expensive, particularly when using transparent substrate materials. For example, fabrication of vias in glass substrates using a powder blasting technique can be challenging to optimize and may result in the weakening of the glass substrate, leading to cracking of the plates during assembly. Fabrication of vias in plastic substrates typically requires micromilling techniques, which tend to be low throughput processes that can become cost-prohibitive when employed in high-volume manufacturing. Injection molding can also be used for fabricating vias, but this process requires a large upfront investment in the micromold master structure. Because vias require strict tolerances on diameter and spacing, any manufacturing process that is employed tends to be expensive, particularly using transparent substrate materials.

The presently disclosed high-throughput microelectrode arrays with flexible circuit array for multilayer interconnect are directed to overcoming one or more of the problems set forth above and/or other problems in the art.

SUMMARY

According to one aspect, the present disclosure is directed to a cell-based biosensor array, comprising a base plate having a plurality of substantially transparent areas and a flexible substrate coupled to the base plate. The flexible substrate may have disposed thereon a plurality of electrode sets, each electrode set disposed proximate a respective one of the substantially transparent areas, wherein each electrode set comprises at least one electrode configured to detect an electric signal. The flexible substrate may also have disposed thereon a plurality of terminal contacts, each terminal contact associated with a respective one of the at least one electrode and disposed proximate a perimeter of the flexible substrate. The flexible substrate may also have disposed thereon a plurality of conductive traces, each conductive trace electrically coupling a respective at least one electrode to the corresponding terminal contact. A first portion of flexible substrate may be disposed on a first surface of the base plate such that the plurality of electrode sets is disposed on the first surface of the base plate. A second portion of the flexible substrate is disposed on a second surface of the base plate such that the plurality of terminal contacts is disposed on the second surface of the base plate.

In accordance with another aspect, the present disclosure is directed to a multiwell microelectrode array, comprising a base plate and a flexible substrate coupled to the base plate. The flexible substrate may have disposed thereon a plurality of electrode sets, each electrode set comprises at least one electrode configured to detect an electric signal associated with biological material located proximate the at least one electrode. The flexible substrate may also have disposed thereon a plurality of terminal contacts, each terminal contact associated with a respective one of the at least one electrode and disposed proximate a perimeter of the flexible substrate. The flexible substrate may also have disposed thereon a plurality of conductive traces, each conductive trace electrically coupling a respective at least one electrode to the corresponding terminal contact. The flexible substrate may be wrapped around at least one edge of the base plate such that the plurality of electrode sets are disposed on a first surface of the base plate and the plurality of terminal contacts are disposed on a second surface of the base plate, the second surface opposing the first surface. The multiwell microelectrode array may also include a plurality of culture wells coupled to the flexible substrate and overlaying at least a portion of the first surface of the base plate, each well disposed proximate a respective one of the electrode sets such that the at least one electrode of the respective one of the electrode sets is configured to detect an electric signal associated with at least a portion of the respective well.

In accordance with another aspect, the present disclosure is directed to a multiwell microelectrode array comprising a substantially transparent base plate and a substantially transparent flexible substrate coupled to the substantially transparent base plate using a substantially transparent adhesive. The substantially transparent flexible substrate having disposed thereon a plurality of electrode sets, each electrode set comprises at least one electrode configured to detect an electrical signal associated with biological material located proximate the at least one electrode. The substantially transparent flexible substrate may also have disposed thereon a plurality of terminal contacts, each terminal contact associated with a respective one of the at least one electrode and disposed proximate a perimeter of the substantially transparent flexible substrate. The substantially transparent flexible substrate may also have disposed thereon a plurality of conductive traces, each conductive trace electrically coupling a respective at least one electrode to the corresponding terminal contact. The flexible substrate is wrapped around at least one edge of the substantially transparent base plate such that the plurality of electrode sets are disposed substantially upon a first surface of the substantially transparent base plate and the plurality of terminal contacts disposed substantially upon a second surface of the substantially transparent base plate, the second surface opposing the first surface.

DETAILED DESCRIPTION

Figure 1:
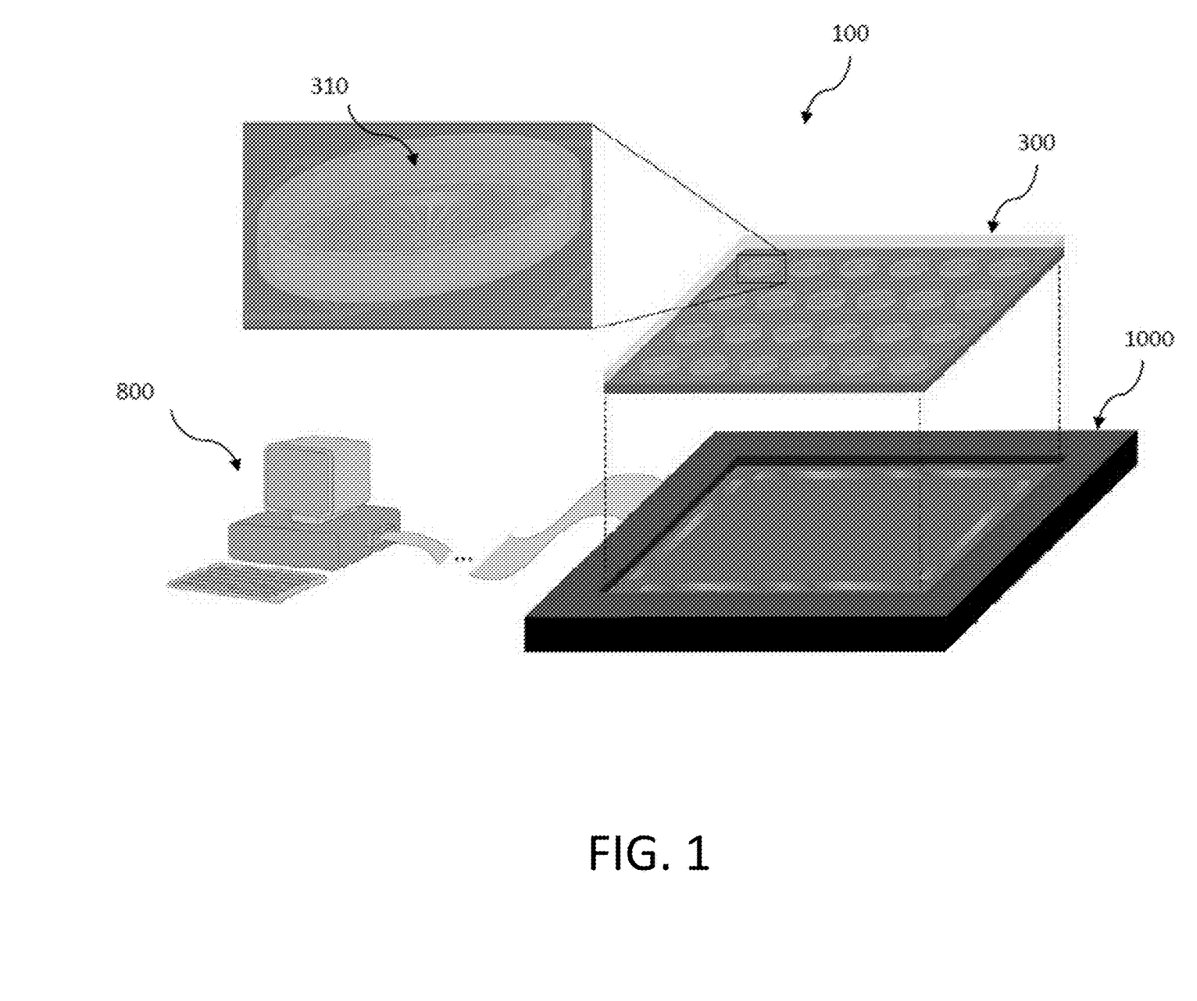
FIG. 1 provides a schematic of a multiwell MEA system for analyzing cell cultures using an American National Standards Institute (ANSI)-Society for Lab Automation and Screening (SLAS) compliant multiwell cell culture array, such as a multiwell microelectrode array (MEA), consistent with certain disclosed embodiments. The figure indicates a multiwell MEA, MEA electronics, and interface to a computer system. A zoomed in view of an individual well is indicated in the inset.

FIG. 1 provides a schematic diagram illustrating a system 100 for analyzing cell cultures using a multiwell microelectrode array (MEA). Importantly, as the terms are used herein, microelectrode array, microsensor array, multiwell MEA, cell-based biosensor array, and multiwell, high-throughput MEA refer to any microelectrode or microsensor array in which the presently-disclosed flexible circuit interconnect design may be implemented. Indeed, those skilled in the art will recognize the presently-disclosed flexible-circuit interconnect embodiments may be beneficial in any microelectrode array system, whether it be a single-well, multi-well, or multiwell, high-throughput MEA format.

According to certain exemplary embodiments, the cell culture analysis system 100 may include a multiwell microelectrode array (MEA) 300 having a plurality of culture wells 310, an MEA plate interface 1000, and a control and monitoring system 800 that is programmed to collect and post-process information detected by the electrodes and (optionally) control electrical stimulation patterns delivered by the electrodes. It is contemplated that additional and/or different components may be included as part of the cell culture analysis system 100 without departing from the scope of the presently disclosed embodiments. For example, system 100 may include an optical recording system for recording images during analysis of the cell cultures.

MEA plate interface 1000 may include or embody any suitable interface for communicatively coupling the presently disclosed multiwell microelectrode array (MEA) with a processor-based computing system 800 having an integrated data analysis and control suite. MEA plate interface may include a plurality of electrical pins configured to align with electrical contacts located on the underside of any ANSI-SLAS compliant multiwell cell culture array. The MEA plate interface is communicatively coupled to control and monitoring system 800 and configured to transfer signals received at the terminal contacts of multiwell MEA to control and monitoring system 800 for analysis.

Control and monitoring system 800 may include or embody any processor-based computing system that is programmed to receive detected data from the MEA, analyze the detected data, and provide a user-interface for viewing the analyzed data and control various aspects of the testing scheme employed by the cell culture analysis system 100. According to one embodiment, control and monitoring system 800 may include one or more hardware components including, for example, a central processing unit (CPU) or microprocessor, a random access memory (RAM) module, a read-only memory (ROM) module, a memory or data storage module, a database, one or more input/output (I/O) devices, and an interface. Alternatively and/or additionally, control and monitoring system 800 may include one or more software media components such as a computer-readable medium including computer-executable instructions for performing methods consistent with certain disclosed embodiments. Control and monitoring system 800 may include additional, fewer, and/or different components than those listed above. It is understood that the components listed above are exemplary only and not intended to be limiting.

Figure 2:
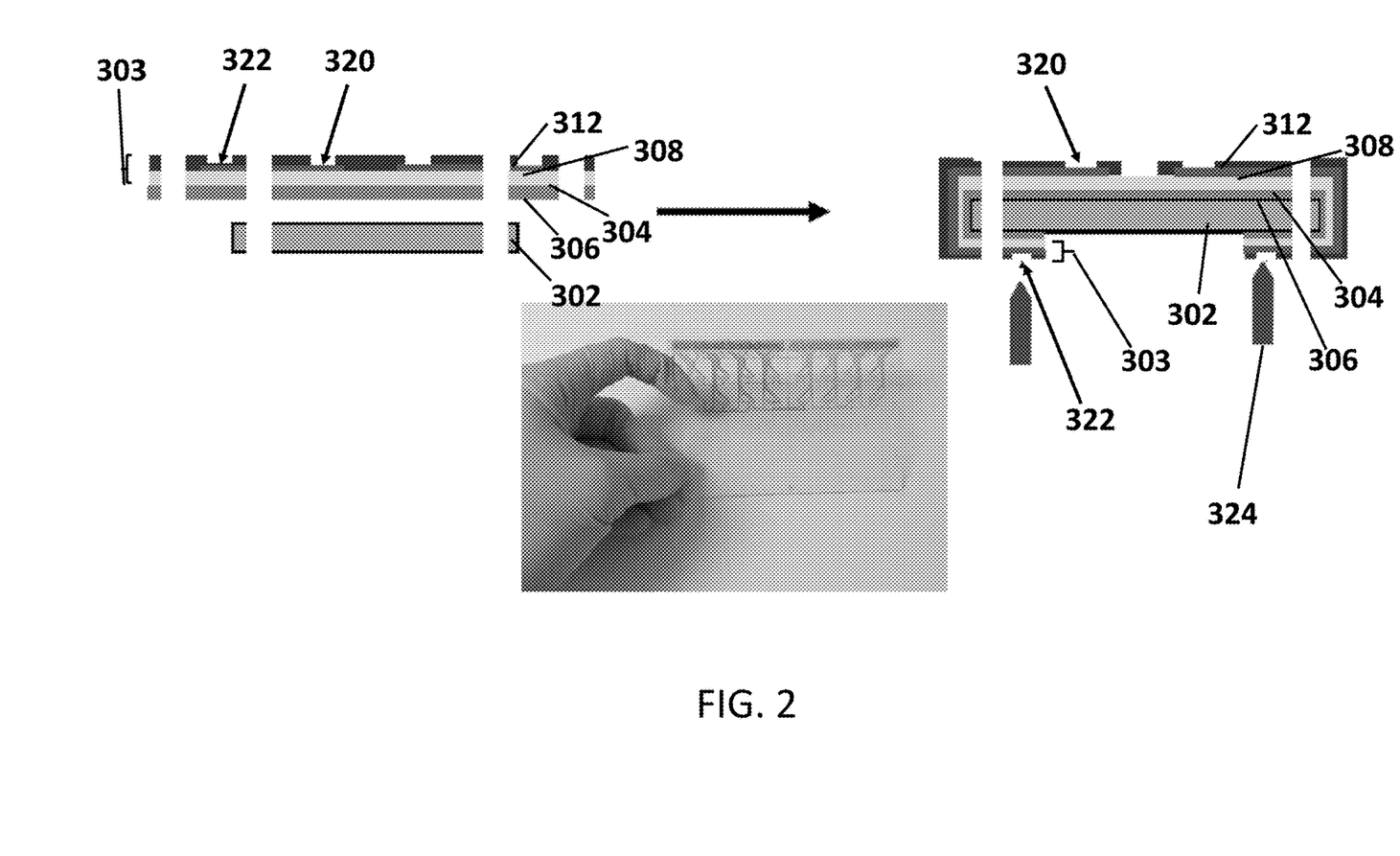
FIG. 2 provides a cross-sectional schematic view of the base plate and single flexible circuit used in the multiwell MEA device, in accordance with certain disclosed embodiments.

Cell culture analysis system 100 may also include a multiwell microelectrode array (MEA) 300. According to one embodiment and as illustrated in FIG. 2, multiwell MEA 300 may comprise a base plate 302, a flexible circuit 303 coupled to the base plate, and a plurality of culture wells (illustrated as element 310 of FIG. 1) coupled to the flexible circuit 303. It is contemplated that multiwell MEA 300 may include additional elements that those listed above. For example, multiwell MEA 300 may include one or more adhesive layers 306 that are used to bond the flexible substrate 304 to the base plate 302 and the culture wells 310 to the flexible substrate 304 (and/or the base plate 302). Multiwell MEA 300 may also include one or more metallic traces 308 and insulation layers 312.

Figure 4:
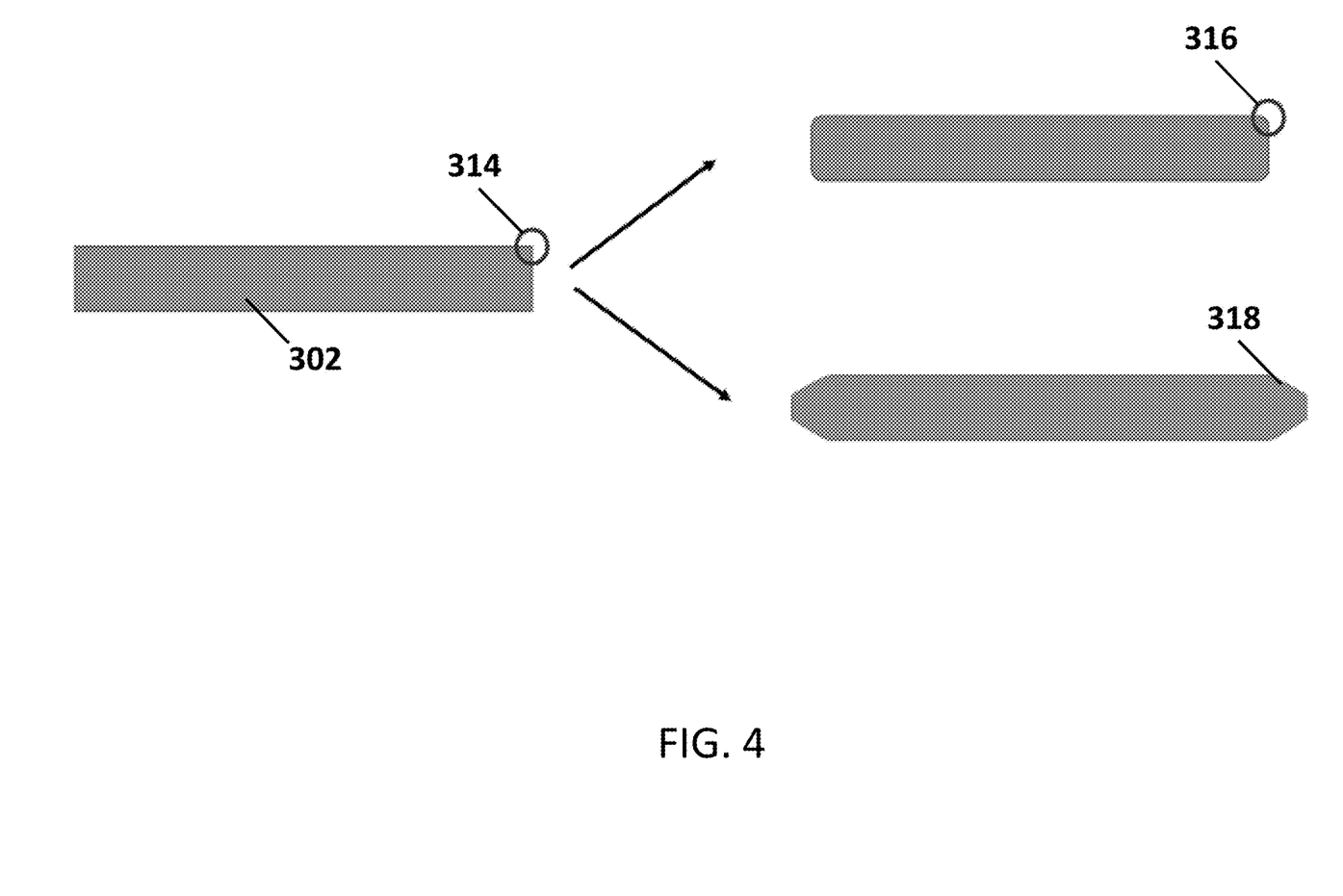
FIG. 4 illustrates a cross-sectional view of the base plate having square (e.g., unsanded), rounded (e.g., sanded), and bull-nosed (e.g., beveled and/or injection molded) edges, consistent with certain disclosed embodiments.

The base plate 302 can be fabricated out of any substantially transparent material. According to one embodiment, the material is inexpensive, robust and can be injection molded (for low cost manufacturing). Many plastics are injection moldable, and hence could be applicable to this process. According to one embodiment, and as illustrated in FIG. 4, one feature to improve the reliability of the MEA plate is beveling the edge 314 of the base plate. The sharp edges of the milled base plates may cause the metal to break at the interface, leading to the metal traces disconnecting at the edge. To avoid the sharp edges, the milled base plate may be sanded with fine grit sand paper to produce a smoother, rounded or sanded edge 316. This smooth edge can be readily achieved in manufacturing with injection molding utilizing techniques such as "bull nosing" to achieve a beveled or bull-nosed edge 318.

The substrate material 304 of the flexible circuit 303 can be made of, but not limited to, acrylic, cyclic olefin copolymer, polycarbonate, polyester, polyetherimide, polyethylene, polyimide, polypropylene, polystyrene, polysulfone, or styrene, or any other transparent plastic or composite material. The substrate can vary in thickness from a micron up to a millimeter.

Figure 5:
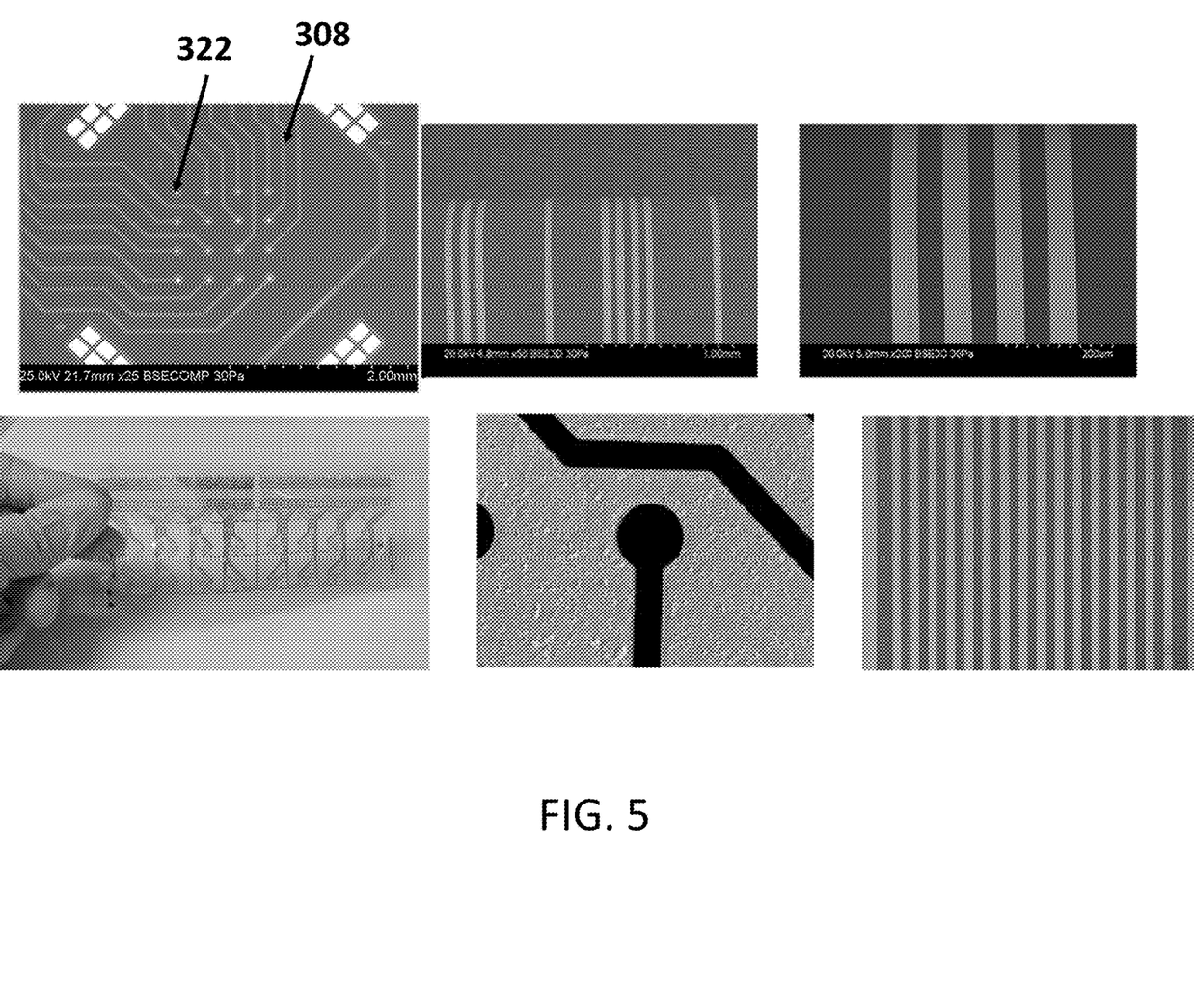
FIG. 5 provides various photograph micrographs and scanning electron micrographs illustrating different features of the fabricated flexible circuits used in the multiwell MEAs, consistent with certain disclosed embodiments. The top three scanning electron microscopy images show the metal on the flexible circuit. The bottom left photograph shows the flexible circuit, and the bottom center and bottom right images show the traces.

As illustrated in FIG. 2, flexible substrate 304 may have disposed thereon a plurality of electrode 320 sets, a plurality of conductive metal traces 308, and a plurality of terminal contacts 322. Each electrode set may comprise at least one electrode 320 configured to detect an electric signal associated with biological material located proximate the at least one electrode. According to one embodiment, multiwell MEA 300 includes a plurality of electrode sets, each electrode set comprises a plurality (e.g., 8) of electrodes, with each set disposed between the substrate 304 and the base of a respective culture well that it is configured to monitor. As illustrated in FIG. 2, flexible substrate 304 may be affixed to a top surface of the base plate 302, such that the electrodes are electrically exposed outwardly from the top surface of the base plate 302. FIG. 5 (photo at top left) illustrates a schematic of an exemplary electrode array.

The conductive metal trace 308 that forms the circuitry may comprise one of several different chemical elements or combinations thereof. According to one exemplary embodiment, the choice of metal, from an applications perspective, may be gold (due to its chemical inertness) with an underlying titanium adhesion layer. However, the metal layer can also include, but is not limited to, titanium, nickel, copper, tin, palladium, silver, or platinum. Other non-metallic materials can also form the conductive circuitry. These materials include, but are not limited to, carbon, graphene, conductive polymers (example, conductive PDMS, PEDOT, etc.) and conducting oxides/nitrides (such as indium tin oxide (ITO) and titanium nitride). The inertness and bio/cytocompatibility of the metal material has to be evaluated and deemed compatible with the various cell lines used in the applications space. Additionally the metal/conductive material chosen needs to satisfy ease of processing and be compatible with the transparent material chosen as the flexible substrate.

The conductive trace 308 can be deposited via electroplating with a seed layer, evaporating, sputtering, electroless plating, atomic monolayer deposition, embossing, self-assembly techniques, etc. There are three primary techniques of depositing the metal onto the surface of the substrate material. The first technique is to do a flood deposition and then etch the pattern into the metal using photoresist. The photoresist acts as a mask and a chemical is used to selectively etch the metal over the photoresist material. The second technique is to use the photoresist as a stencil, deposit the metal, and then remove the resist, thereby leaving the patterned metal on the surface. Microstenciling can additionally be used as a technique to deposit the metal. In this technique, the stencil can be reused as opposed to a resist stencil. The third technique is to define areas where metal is to be defined with a photoresist lithography technique. Deposit metal everywhere and lift-off areas where metal is not required. Metal lift-off is achieved due to the photolithography step defining the metal area but leaving the photoresist in place. There are several other techniques for defining a metal layer such as electroplating, electroless plating, embossing etc.

As shown in FIG. 5, electrode arrays are made up of a grid of tightly spaced electrodes 322, and each electrode is capable of simultaneously monitoring the activity of individual cells. The arrangement of multiple electrodes in a grid extends the recording range across a relatively large area, providing concurrent access to both single cell and tissue- or network-level activity. The control and monitoring of this cellular activity is made possible by the electronics, which impart multiple functions to each electrode.

Each electrode of the array facilitates monitoring of single-cell and network-level activity for extended periods of time, with virtually no destructive interference to the tissue being investigated. In fact, the broad access to network information along with the minimally invasive nature of the device is precisely what makes the MEA an exemplary single-cell and cellular network-level research tool. Each electrode in the high throughput MEA is ideally suited for investigation of electroactive cells and tissue (e.g., neural, cardiac, muscle, and spinal tissue). As explained previously, the MEA-wells are organized in an ANSI-SLAS compliant format, compatible with traditional plate readers and automated instrumentation. Within each well, a plurality (e.g., between 4 and 64) of individual embedded microelectrodes (~30-50 µm diameter; ~200-350 µm center-to-center spacing, in accordance with an exemplary embodiment) with integrated ground (or reference) electrodes are capable of simultaneously monitoring the activity of individual cells. The arrangement of these electrodes into a grid extends the recording range up to approximately 1.5×1.5 mm area, providing concurrent access to both single-cell and network-level activity.

Each of the electrodes in every set of the plurality of electrodes may be configured to simultaneously provide stimulation to the cells in the culture well and record electric signals resulting from stimulation of the cells. Alternatively or additionally, some of the electrodes in the set may be configured to provide stimulation only, while other electrodes are dedicated to recording cellular activity.

Flexible substrate 304 may also have disposed thereon a plurality of terminal contacts 322, each terminal contact associated with a respective one of the at least one electrode 320 and disposed proximate a perimeter of the flexible substrate. As illustrated in FIG. 2, terminal contacts 322 may be disposed on the perimeter portion of the flexible substrate 304, which is wrapped around at least one edge of the base plate 302. After wrapping, the terminal contact is affixed to a different surface (e.g., bottom or side) of base plate 302 relative to the electrodes 320.

Flexible substrate 304 may also have disposed thereon a plurality of conductive traces 308, each conductive trace electrically coupling a respective at least one electrode 320 to the corresponding terminal contact 322. Pogo pins 324 may be used to connect to terminal contacts 322 and transmit an electrical signal. Pogo pins 324 may be spring loaded or otherwise movable such that the terminal contacts 322 securely contact the pogo pins 324 without applying too much force to damage the terminal contacts 322.

The flexible substrate may also include a substantially transparent insulating layer 312 disposed over the plurality of conductive traces 308 and configured to electrically isolate the plurality of conductive traces from one another. To ensure electrical access to the terminal contacts 322 and electrode 320 arrays, the insulating layer is not defined over the terminal contacts and electrode arrays. There are several choices for the insulating material. The insulation layer may be configured to insulate each trace and to define the microelectrodes. Additionally, this layer supports biomolecular coatings and cellular cultures. The microfabrication processes used to define this layer can include, but not limited to, the following techniques: photolithography, lamination, embossing, laser micromachining, deposition and etch, selective deposition utilizing a sacrificial material, etc. According to one embodiment, the insulating material may be the same material as the substrate 304 material to provide comparable coefficient of thermal expansions and other comparable properties (such as material stiffness, yield strength, dielectric constant, biological compatibility, chemical resistance etc.) but material matching may not be possible in all fabrication processes. Possible insulation materials can include, but are not limited to, all the plastics mentioned in the substrate materials paragraph (above), as well as SU-8, parylene, polyimide, and the like.

The adhesive 306 is used to attach the flexible circuit 303 to the base plate 302. These adhesives include, but are not limited to, epoxies, double-sided tape, acrylic-based, solvent-bondable, reflow, optically clear adhesives (OCA) or pressure sensitive adhesives (PSA). There are also other methods of attaching the flexible circuit 303 to the base plate 302 such as, but not limited to, solvent bonding, thermal bonding, UV bonding, etc. According to certain embodiments, the adhesive layer may be substantially transparent, bio/cytocompatible, or both. Regarding transparency, a parameter to analyze is the index of refraction. The index of refraction of optically clear adhesives is typically matched to glass or plastic (1.49-1.57), thereby providing an exceptionally transparent material. The index of SU-8 is in the range of 1.59-1.67. The thickness of the adhesive has to be considered as well and can contribute towards the overall transparency. Adhesives can vary from less than a micron up to 1 millimeter in thickness.

According to one exemplary embodiment, the plurality of culture wells may be coupled to the substantially transparent flexible substrate and overlay at least a portion of the first surface of the substantially transparent base plate. Each well disposed proximate a respective one of the electrode sets such that the at least one electrode of the respective one of the electrode sets is configured to detect an electric signal associated with at least a portion of the respective well. It should be noted that the culture wells, being described in an exemplary embodiment as being located "proximate" the electrodes, can be located relative to the electrodes such that the electrodes can detect cellular activity associated with a respective well. Thus, culture wells can be located above, next to, near, or adjacent to, electrode sets.

Exemplary Fabrication Method

Figure 3:
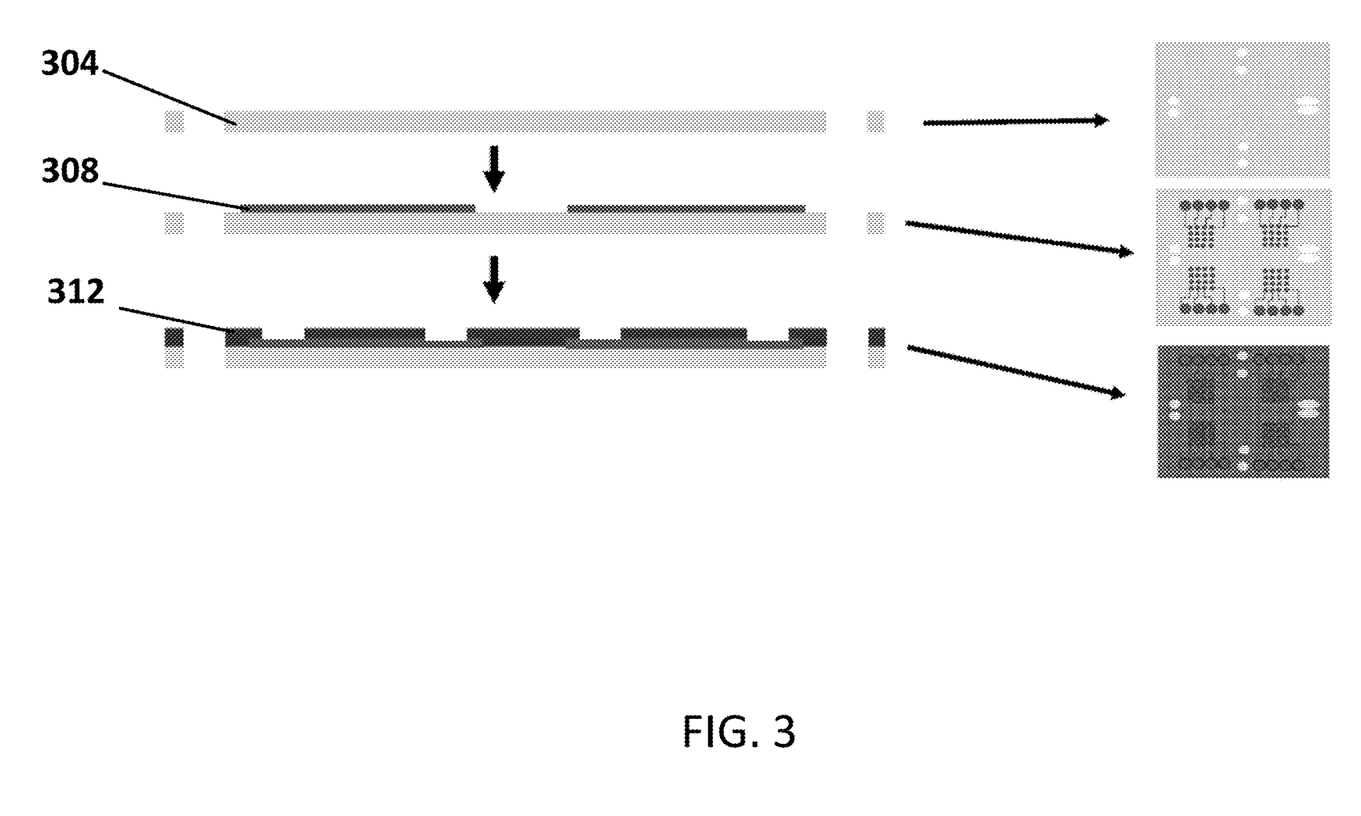
FIG. 3 provides cross-sectional and top views of a flexible circuit for the multiwell MEA system during various stages of processing, in accordance with the disclosed embodiments.

The material set may be selected for optimal yield, ease of processing, and durability. The substrate material of the flexible circuit may consist of a 36 µm thick layer of PET with a proprietary transparent adhesive. The metal layer consists of 3 µm nickel and 0.2 µm gold. This layer is defined photolithographically and subsequently embossed in a 3 µm thick SU-8 layer. The flexible circuit is subsequently completed by applying a 3-5 µm thick SU-8 overcoat (insulation material). This material insulates the traces and defines the microelectrodes. Once the flexible circuit is fabricated, it is accurately attached to a CNC micromilled polycarbonate base plate with an adhesive layer (3M 8211 OCA) as described below. FIG. 3 depicts the process flow for the fabrication of the flexible circuit. FIG. 5 depicts scanning electron and optical micrographs of completed devices.

Exemplary Assembly of the High-Throughput Transparent MEA (tMEA)

Schematic of the assembly process and an assembled flexible circuit on a base plate are shown in FIG. 2. Assembling the base plate to the flexible circuit with the optically clear adhesive, and ultimately to a culture well plate, requires extremely accurate mechanical jigs. These jigs are designed in 3-D CAD (e.g. Creo) and fabricated on materials such as aluminum utilizing technologies such as water jet cutting. The base plate, flexible circuit, and OCA have precisely located, identical features that serve as alignment fixtures. These fixtures enable an alignment accuracy of ±50 microns. The mechanical jigs consist of extruded pins that align to the fixtures in the materials enabling relatively simple alignment.

The first step in assembling the tMEA is applying the OCA film to the base plate. The OCA film is secured on both sides with a PET release layer. This layer serves as a protective film for the OCA. Alignment is performed with the following steps: (a) the adhesive is attached to the alignment jig with the release layers intact; (b) the base plate is subsequently aligned to the OCA (release layer on the topside is removed) using the three alignment pins. This step is performed for both halves of the circuit; (c) the flexible circuit is further applied to the OCA covered base plate. Both halves of the flexible circuit are aligned in this manner. Once the flexible circuit is attached to the baseplate the MEA plate is assembled and in order to secure the assembly, a pressure of one metric ton is uniformly applied to the device utilizing a lamination press (no heat is involved in this process). This pressure cycle ensures that the flexible circuit is firmly attached to the base plate and eliminates any bubbles that could have formed in the OCA layer. To complete the assembly, a culture well plate (a bottomless microtiter plate modified to accommodate a MEA plate on the bottom-side) is applied to the aforementioned MEA plate through a sequence of precise alignment steps utilizing an intermediate layer of pressure sensitive adhesive (PSA). Such culture well plates are designed utilizing 3-D CAD software such as Creo and fabricated utilizing processes such as injection molding or micromilling.

Exemplary Noise Profiles

Figure 6:
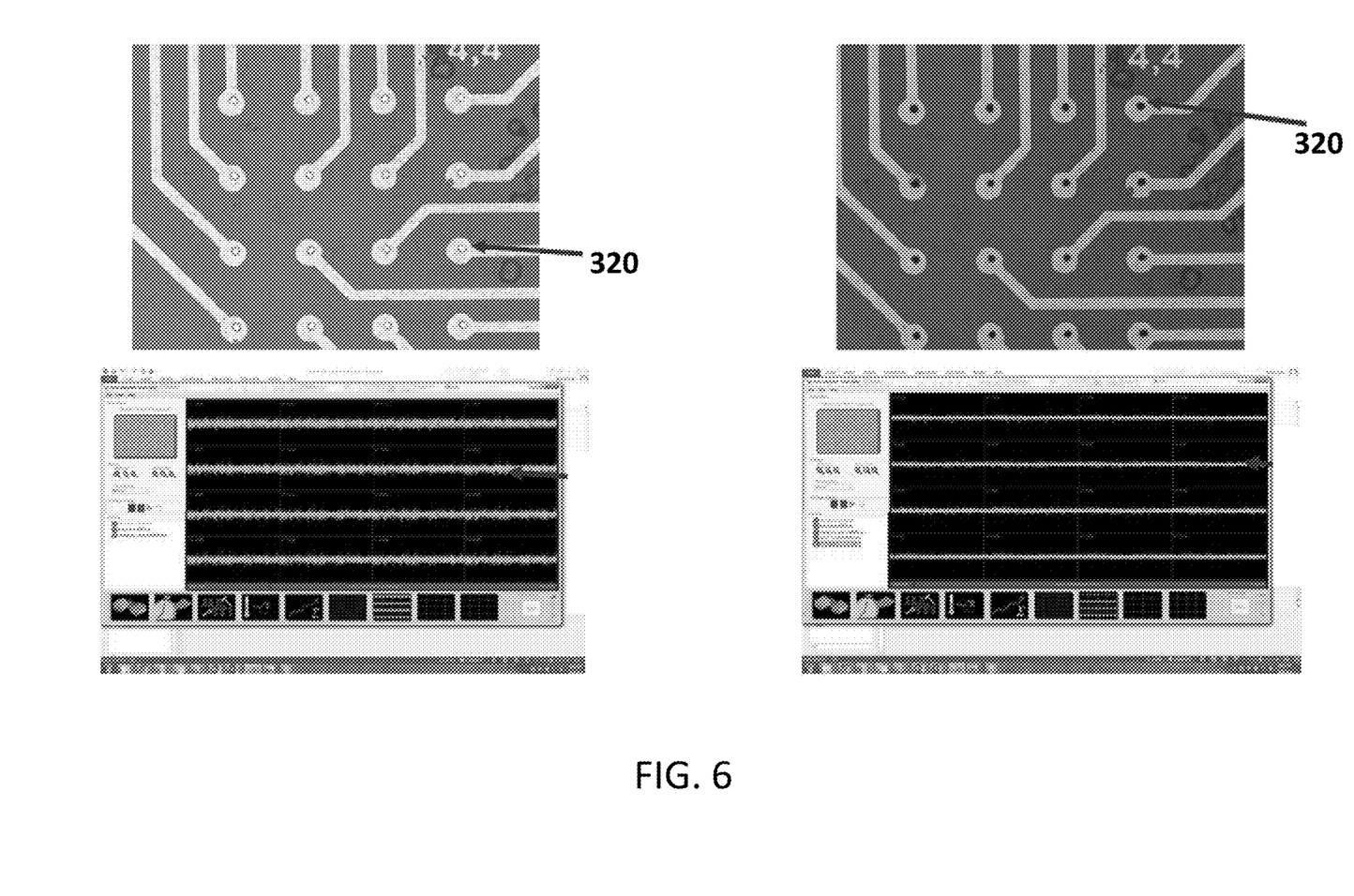
FIG. 6 provides images showing different noise profiles for electrodes made of gold and nano-porous platinum, consistent with certain disclosed embodiments. The top left photograph shows a culture well with gold electrodes. The bottom left shows the RMS noise associated with the culture well having gold electrodes (RMS noise>10 µV). The top right photograph shows a culture well with nano-porous platinum electrodes. The bottom right shows the RMS noise associated with the culture well having nanoporous platinum electrodes (RMS noise<8 µV).

FIG. 6 provides images showing different noise profiles for electrodes made of gold and nano-porous platinum, consistent with certain disclosed embodiments. The top left photograph shows a single well with gold electrodes. The bottom left shows the RMS noise associated with the culture well having gold electrodes (RMS noise>10 µV). The top right photograph shows a single well with nano-porous platinum electrodes. The bottom right shows the RMS noise associated with the culture well having nano-porous platinum electrodes (RMS noise<8 µV).

Exemplary Impedance Measurements

Figure 7:
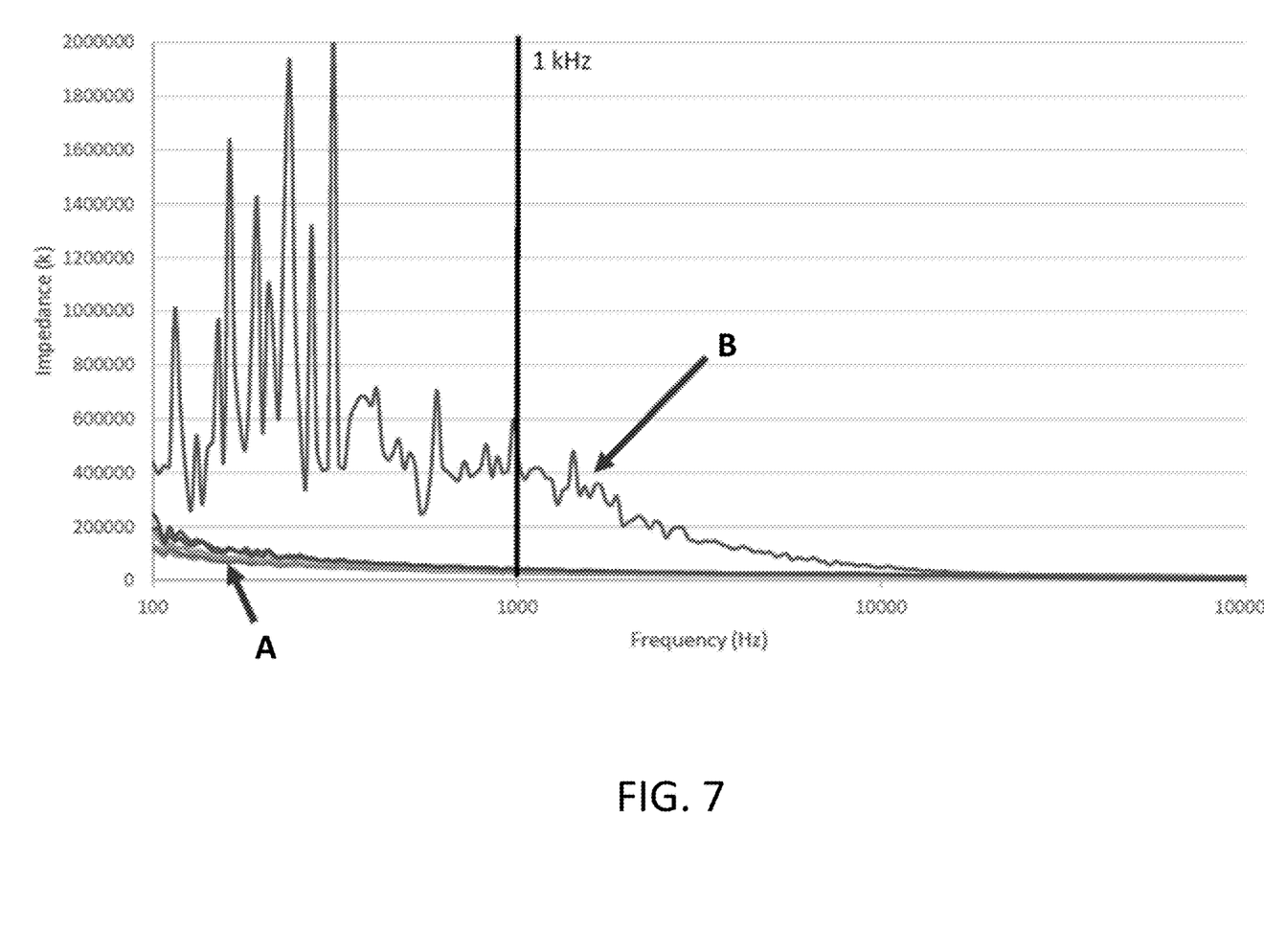
FIG. 7 provides a full frequency spectrum impedance chart for functional (A) and non-functional (B) microelectrodes having nano-porous platinum electrodes, in accordance with certain disclosed embodiments.

FIG. 7 provides a full frequency spectrum impedance chart for functional (A) and non-functional (B) microelectrodes having nano-porous platinum electrodes, in accordance with certain disclosed embodiments.

Exemplary Stress Testing

Figure 8:
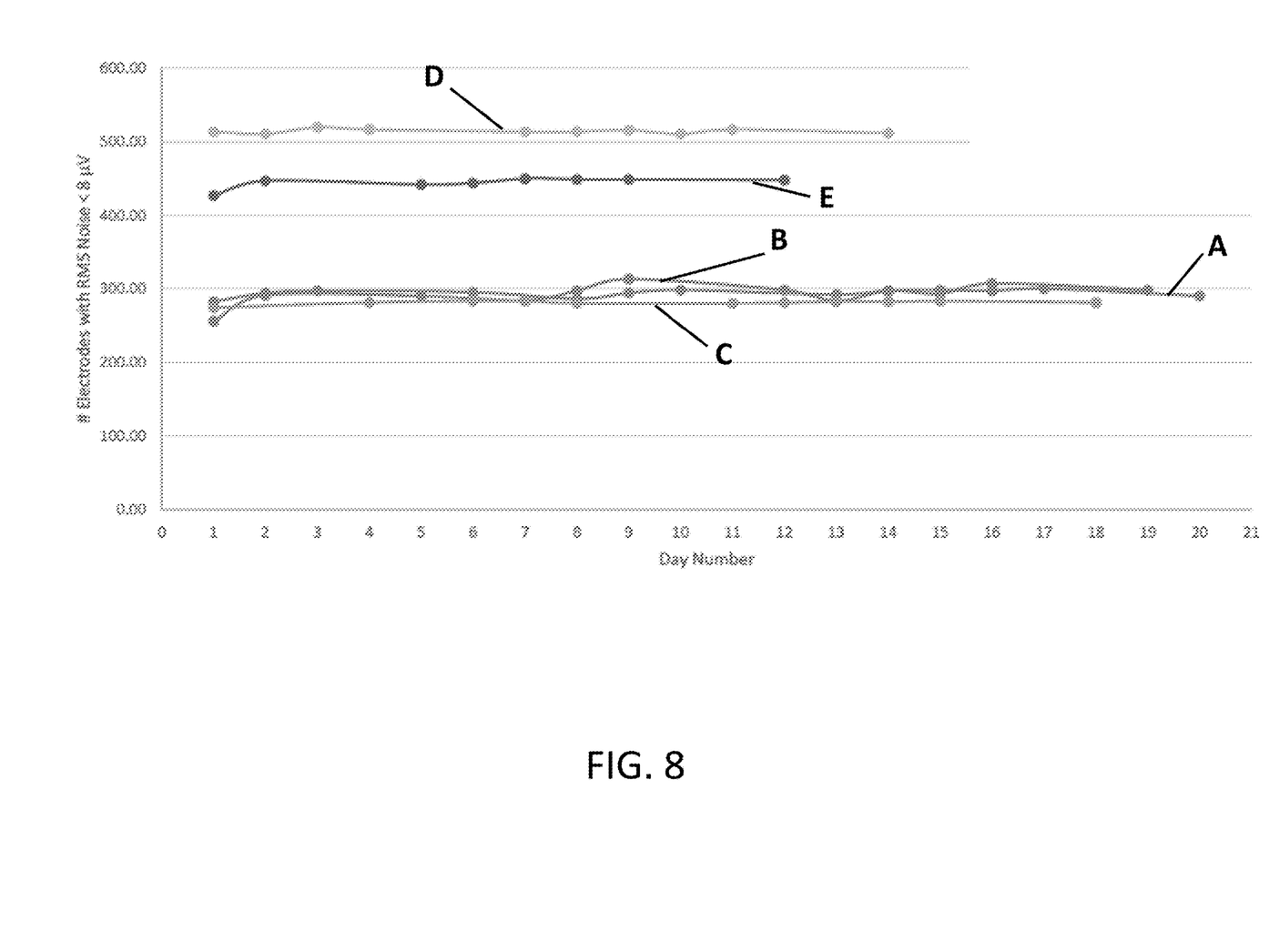
FIG. 8 provides a chart showing electrical root mean square (RMS) noise tracking across five different sample devices (samples A-E) subjected to mechanical stress applied on the devices with the Maestro multiwell MEA system and thermal/fluidic stress applied in an incubator in accordance with the disclosed embodiments after multiday usage.

FIG. 8 shows electrical root-mean-square (RMS) noise (measured in microvolts) tracking across five different exemplary sample devices subjected to mechanical stress applied on the devices with the multiwell MEA system and thermal/fluidic/humidity stressors applied on the devices utilizing an incubator in accordance with the disclosed embodiments after multiday usage. Particularly, the chart of FIG. 8 shows the number of electrodes per device with RMS noise of less than 8 µV and tracks this noise metric across the devices for 21 days (typical time of a neural cell culture). Table 1 below shows the following metrics for the five exemplary devices: i) optical yield (measuring nano-porous platinum optically across all electrodes—768 per device), ii) electrical yield (number of microelectrodes with less than 8 µV RMS noise), and iii) electrode difference (the difference of electrodes having noise <8 µV on the first day versus the last day of testing).

TABLE 1

| Sample | A | B | C | D | E |
|---|---|---|---|---|---|
| Optical Yield | 92.50% | 56.00% | 69.40% | 69.40% | 71.50% |
| Electrical Yield | 88.90% | 52.10% | 66.10% | 70.60% | 53.80% |
| Electrode difference | −4 | 7 | 0 | 1 | 1 |

Exemplary ATP Assay

Figure 9:
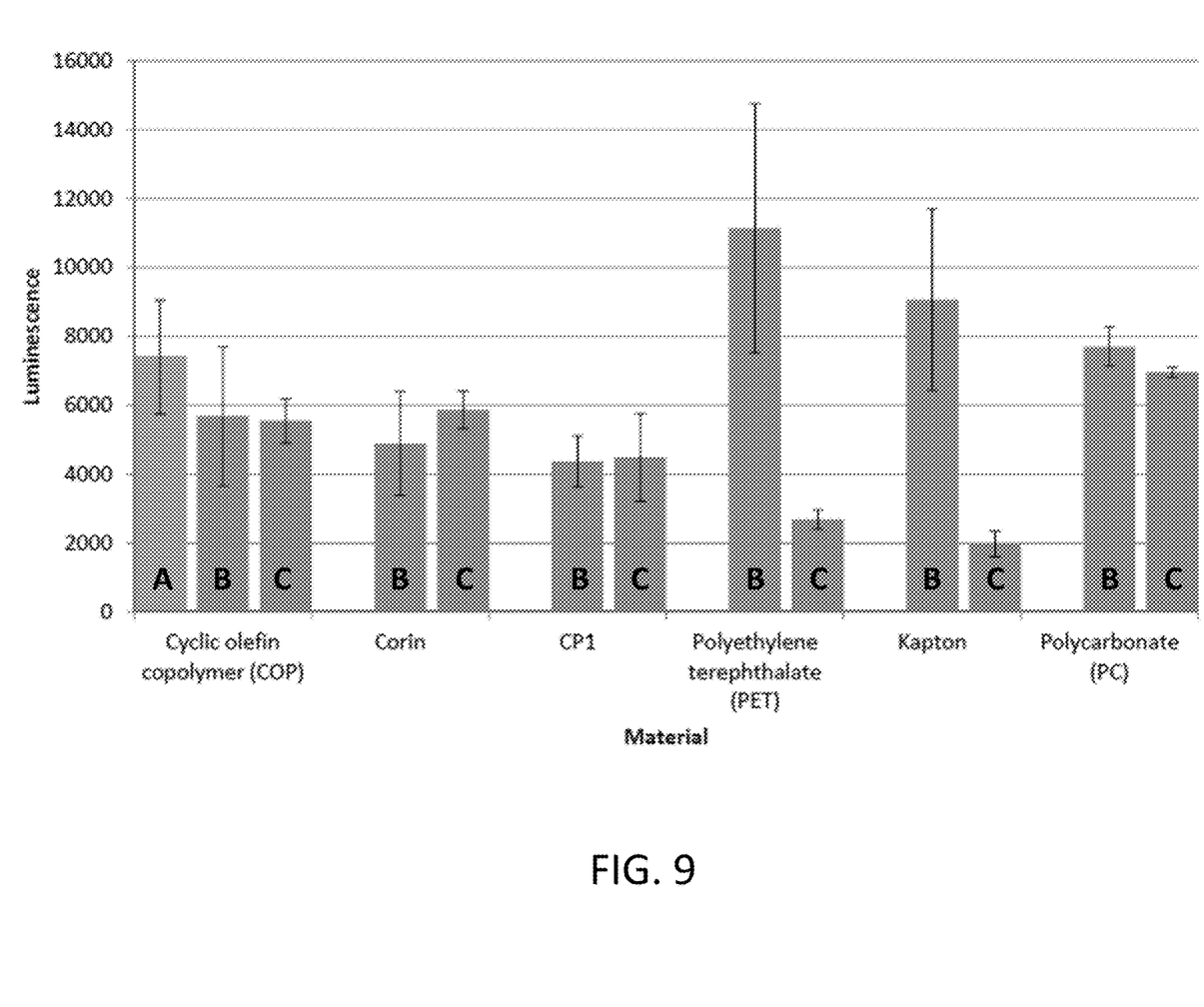
FIG. 9 provides a chart showing ATP assay results for the various MEA insulation materials manufactured in accordance with the disclosed embodiments. The labelling on the chart corresponds to: (A) flexible circuit, (B) native material, and (C) laser drilled.

FIG. 9 provides a chart showing ATP assay results for the various MEA insulation materials manufactured in accordance with the disclosed embodiments. The labels correspond to: (A) flexible circuit, (B) native material, (C) laser drilled. The ATP assay is an excellent measure of the cytocompatibility of the materials with respect to neuronal cultures. This assay can be a homogeneous method for determining the number of viable cells in culture based on the quantification of the Adinosine Tri-Phosphate (ATP) present. ATP is regarded as a well-established indicator of metabolically active cells. The CellTiter-Glo® Assay can be designed for use with high-throughput formats, making it ideal for automated high-throughput screening (HTS), cell proliferation and cytotoxicity assays. The homogeneous assay procedure can involve adding the single reagent (CellTiter-Glo® Reagent) directly to cells cultured in serum-supplemented medium. Cell washing, removal of medium and multiple pipetting steps are not required. The assay system is capable of detecting as few as 15 cells/well in a 384-well format in 10 minutes after adding reagent and mixing. As seen in FIG. 9 the various insulation materials perform as well as the control Polycarbonate substrate depicting excellent cytocompatibility with respect to neuronal cell cultures.

It will be apparent to those skilled in the art that various modifications and variations can be made to the disclosed transparent multiwell microelectrode arrays employing flexible circuits for implementing multilayer interconnects. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A cell-based biosensor array, comprising:
   a base plate, having a plurality of substantially transparent areas;
   a flexible substrate having a first surface and a second surface that opposes the first surface, the second surface of the flexible substrate being coupled to the base plate, and the first surface of the flexible substrate having disposed thereon:
      a plurality of electrode sets, each electrode set disposed proximate a respective one of the substantially transparent areas, wherein each electrode set comprises at least one electrode configured to detect an electric signal;
a plurality of terminal contacts, each terminal contact associated with a respective one of the at least one electrode and disposed proximate a perimeter of the flexible substrate; and
a plurality of conductive traces, each conductive trace electrically coupling a respective at least one electrode to the corresponding terminal contact;
wherein a first portion of flexible substrate is disposed on a first surface of the base plate such that the plurality of electrode sets are disposed on the first surface of the base plate, and
wherein a second portion of the flexible substrate is disposed on a second surface of the base plate such that the plurality of terminal contacts are disposed on the second surface of the base plate, wherein at least a portion of an edge of the base plate around which the flexible substrate is wrapped is rounded or beveled.

2. The device of claim 1, further comprising:
a plurality of culture wells coupled to the flexible substrate and overlaying at least a portion of the first surface of the base plate, each culture well disposed proximate a respective one of the electrode sets such that the at least one electrode of the respective one of the electrode sets is configured to detect an electric signal associated with at least a portion of the respective culture well.

3. The device of claim 1, wherein the base plate and the flexible substrate are substantially transparent.

4. The device of claim 3, wherein the base plate and the flexible substrate are constructed of a transparent material comprising at least one of acrylic, cyclic olefin copolymer, polycarbonate, polyester, polyetherimide, polyethylene, polyimide, polypropylene, polystyrene, polysulfone, or styrene.

5. The device of claim 3, wherein the flexible substrate is coupled to the base plate using a substantially transparent adhesive that is substantially matched to an index of refraction of the base plate and the flexible substrate.

6. The device of claim 1, wherein the flexible substrate includes a substantially transparent insulating layer disposed over the plurality of conductive traces and configured to electrically isolate the plurality of conductive traces from one another.

7. The device of claim 6, wherein the insulating layer is not disposed over the terminal contacts or the electrode sets.

8. The device of claim 1, wherein the at least one electrode is further configured to deliver electric stimulation.

9. The device of claim 1, further comprising a second electrode configured to detect an electric signal.

10. The device of claim 9, wherein the second electrode is further configured to deliver electric stimulation.

11. The device of claim 1, wherein the plurality of electrode sets are electrically exposed outwardly from the first surface of the base plate and the plurality of terminal contacts are electrically exposed outwardly from the second surface of the base plate.

12. The device of claim 1, wherein the second surface of the base plate opposes the first surface of the base plate.

13. A multiwell microelectrode array, comprising:
a base plate;
a flexible substrate having a first surface and a second surface that opposes the first surface, the second surface of the flexible substrate being coupled to the base plate, and the first surface of the flexible substrate having disposed thereon:
a plurality of electrode sets, each electrode set comprises at least one electrode configured to detect an electric signal associated with biological material located proximate the at least one electrode;
a plurality of terminal contacts, each terminal contact associated with a respective one of the at least one electrode and disposed proximate a perimeter of the flexible substrate; and
a plurality of conductive traces, each conductive trace electrically coupling a respective at least one electrode to the corresponding terminal contact;
wherein the flexible substrate is wrapped around at least one edge of the base plate such that the plurality of electrode sets are disposed on a first surface of the base plate and the plurality of terminal contacts are disposed on a second surface of the base plate, wherein at least a portion of the at least one edge of the base plate is rounded or beveled; and
a plurality of culture wells coupled to the flexible substrate and overlaying at least a portion of the first surface of the base plate, each culture well disposed proximate a respective one of the electrode sets such that the at least one electrode of the respective one of the electrode sets is configured to detect an electric signal associated with at least a portion of the respective culture well.

14. The multiwell microelectrode array of claim 13, wherein the base plate comprises a plurality of substantially transparent areas, each of the substantially transparent areas disposed proximate a bottom portion of a respective one of the culture wells such that the respective culture well is visible through the base plate.

15. The multiwell microelectrode array of claim 13, wherein a thickness of the base plate is between about 0.30 mm and about 3.00 mm.

16. The multiwell microelectrode array of claim 13, wherein a thickness of the flexible substrate is between about 0.005 mm and about 0.250 mm.

17. A multiwell microelectrode array, comprising:
a substantially transparent base plate;
a substantially transparent flexible substrate having a first surface and a second surface that opposes the first surface, the second surface of the substantially transparent flexible substrate being adhesively coupled to the substantially transparent base plate using a substantially transparent adhesive, the first surface of the substantially transparent flexible substrate having disposed thereon:
a plurality of electrode sets, each electrode set comprises at least one electrode configured to detect an electric signal associated with biological material located proximate the at least one electrode;
a plurality of terminal contacts, each terminal contact associated with a respective one of the at least one electrode and disposed proximate a perimeter of the substantially transparent flexible substrate; and
a plurality of conductive traces, each conductive trace electrically coupling a respective at least one electrode to the corresponding terminal contact;
wherein the substantially transparent flexible substrate is wrapped around at least one edge of the substantially transparent base plate such that the plurality of electrode sets are disposed substantially upon a first surface of the substantially transparent base plate and the plurality of terminal contacts disposed substantially upon a second surface of the substantially transparent base plate, the second surface opposing the first surface, wherein at least a portion of the at least one edge of the substantially transparent base plate is rounded or beveled.

18. The multiwell microelectrode array of claim 17, further comprising a plurality of culture wells coupled to the substantially transparent flexible substrate and overlaying at least a portion of the first surface of the substantially transparent base plate, each culture well disposed proximate a respective one of the electrode sets such that the at least one electrode of the respective one of the electrode sets is configured to detect an electric signal associated with at least a portion of the respective culture well.

* * * * *